(12) United States Patent
Pagani et al.

(10) Patent No.: US 9,074,207 B2
(45) Date of Patent: Jul. 7, 2015

(54) MODIFIED HUMAN U1SNRNA MOLECULE, A GENE ENCODING FOR THE MODIFIED HUMAN U1SNRNA MOLECULE, AN EXPRESSION VECTOR INCLUDING THE GENE, AND THE USE THEREOF IN GENE THERAPY

(75) Inventors: Franco Pagani, Monfalcone (IT); Mirko Pinotti, Ferrara (IT)

(73) Assignee: UNIVERSITA' DEGLI STUDI DI FERRARA, Ferrara (IT)

( * ) Notice: Subject to any disclaimer, the term of this patent is extended or adjusted under 35 U.S.C. 154(b) by 0 days.

(21) Appl. No.: 13/878,355

(22) PCT Filed: Oct. 14, 2011

(86) PCT No.: PCT/IB2011/054573
§ 371 (c)(1),
(2), (4) Date: Apr. 8, 2013

(87) PCT Pub. No.: WO2012/049665
PCT Pub. Date: Apr. 19, 2012

(65) Prior Publication Data
US 2013/0210902 A1    Aug. 15, 2013

(30) Foreign Application Priority Data
Oct. 15, 2010   (IT) .............................. TO2010A0840

(51) Int. Cl.
C07H 21/04   (2006.01)
C12N 15/113  (2010.01)
C12N 15/11   (2006.01)

(52) U.S. Cl.
CPC ............ *C12N 15/113* (2013.01); *C12N 15/111* (2013.01); *C12N 15/1137* (2013.01); *C12N 15/1138* (2013.01); *C12N 2310/11* (2013.01); *C12N 2320/33* (2013.01); *C12N 2330/51* (2013.01); *C12Y 304/21022* (2013.01); *C12Y 306/03049* (2013.01)

(58) Field of Classification Search
None
See application file for complete search history.

(56) References Cited

U.S. PATENT DOCUMENTS

| | | | |
|---|---|---|---|
| 2002/0058287 A1 | 5/2002 | Graaf et al. | |
| 2010/0087511 A1 | 4/2010 | Singh et al. | |
| 2010/0216238 A1* | 8/2010 | Baker et al. | 435/375 |

FOREIGN PATENT DOCUMENTS

WO    2007/002390 A2    1/2007

OTHER PUBLICATIONS

Marquis et al. (Molecular Therapy, 2007, vol. 15:1479-1486).*
Gorman, Linda, et al.: "Restoration of correct splicing of thalassemic beta-globin pre-mRNA by modified U1 snRNAs", Journal of Biological Chemistry, vol. 275, No. 46, Nov. 2000, pp. 35914-35919, the whole document.
Buratti, Emanuele, et al.: "SR protein-mediated inhibition of CFTR exon 9 inclusion: molecular characterization of the intronic splicing silencer", Nucleic Acids Research, vol. 35, No. 13, 2007, pp. 4359-4368, the whole document.
Dhir, Ashish and Buratti, Emanuele: "Alternative splicing: role of pseudoexons in human disease and potential therapeutic strategies", FEBS Journal, vol. 277, No. 4, Feb. 2010, pp. 841-855, the whole document.
Kato, K., et al.: "Hyperstable U1snRNA complementary to the K-ras transcripts induces cell death in pancreatic cancer cells", British Journal of Cancer, vol. 87, No. 8, Oct. 7, 2002, pp. 898-904, the whole document.
Incitti, Tania, et al.: "Exon skipping and duchenne muscular dystrophy therapy: Selection of the most active U1 snRNA-antisense able to induce Dystrophin exon 51 skipping", Molecular Therapy, vol. 18, No. 9, Sep. 1, 2010, pp. 1675-1682, DOI:10.1038/MT.2010.123 [retrieved on Jun. 15, 2010], the whole document.
De Angelis, Fernanda Gabriella, et al.: "Chimeric snRNA molecules carrying antisense sequences against the splice junctions of exon 51 of the dystrophin pre-mRNA induce exon skipping and restoration of a dystrophin synthesis in Delta 48-50 DMD cells", Proceedings of the National Academy of Sciences of the United States (PNAS), vol. 99, No. 14, Jul. 9, 2002, pp. 9456-9461, DOI:DOI:10.1073/PNAS. 142302299 [retrieved on Jun. 20, 2002], the whole document.
Denti, Michela Alessandra, et al.: "Chimeric adeno-associated virus/ antisense U1 small nuclear RNA effectively rescues dystrophin synthesis and muscle function by local treatment of mdx mice", Human Gene Therapy, vol. 17. No. 5. May 2006, pp. 565-574, the whole document.
Garcia-Blanco, Mariano A., et al.: "Alternative splicing in disease and therapy", Nature Biotechnology, vol. 22, No. 5, May 2004, pp. 535-546, the whole document.
Garcia-Blanco, Mariano A., et al.: "Alternative splicing in disease and therapy—Supplementary Information", May 2004, retrieved from the Internet: URL:http://www.nature.com/nbt/journal/v22/n5/suppinfo/nbt964_SI.html [retrieved on May 18, 2011], the whole document.
Nlend Nlend, Rachel, et al.: "Repair of pre-mRNA splicing. Prospects for a therapy for Spinal Muscular Atrophy", RNA Biology, vol. 7, No. 4, Jul. 2010, pp. 430-440, the whole document.
Singh, Natalia N., et al.: "Modulating role of RNA structure in alternative splicing of a critical exon in the spinal muscular atrophy genes", Nucleic Acids Research, vol. 35, No. 2, Jan. 2007, pp. 371-389, figure 3.

(Continued)

*Primary Examiner* — Kimberly Chong
(74) *Attorney, Agent, or Firm* — Lucas & Mercanti, LLP

(57) ABSTRACT

A modified human U1snRNA molecule is described, the target sequence of which is located in a region of the pre-mRNA of the target gene comprised between 2 and 50 base pairs downstream of an exon/intron junction site, which is capable of restoring the correct splicing of a target gene of therapeutic interest bearing a mutation which induces exon skipping and resulting in a genetic disease. Modified human U1snRNA molecules are described by way of example for the correction of diseases associated with exon skipping, such as spinal muscular atrophy, hemophilia B, and cystic fibrosis.

14 Claims, 15 Drawing Sheets

(56) References Cited

OTHER PUBLICATIONS

Pagani, Franco, et al.: "A new type of mutation causes a splicing defect in ATM", Nature Genetics, vol. 30, No. 4, Apr. 2002, pp. 426-429, the whole document.

Lund, E., et al.: "True genes for human U-1 small nuclear RNA. Copy number, polymorphism and methylation", Journal of Biological Chemistry, vol. 259, No. 3, 1984, pp. 2013-2021, the whole document.

Montgomery, R.A., et al.: "Inhibition of fibrillin 1 expression using U1 snRNA as a vehicle for the presentation of antisense targeting sequence", Human Molecular Genetics, vol. 6, No. 4, 1997, pp. 519-525, the whole document.

Le Roy, F., et al.: "RNA-targeting approaches for neuromuscular diseases", Trends in Molecular Medicine, vol. 15, no. 12, Dec. 2009, pp. 580-591, the whole document.

\* cited by examiner

```
                                                       fix22
                                              fix16
                                            fix13
                                           fix10
                                          fix9
                                         fix7                              fix38
                                                                    fix33
                                  fix1
                      fix-7
CCAGCAGgtcataatctgaataagattttaaagaaaatctgtatctgaaacttcagcattttaacaaacctacat
                                                                                    fix63
```

Figure 5

```
                    -1G-2G-3A
                  ─────────────
                              SH2                    SH17
                           ──────              ──────────
     TAAGGA gtaagtctgccagcattatgaaagtgaatcttactttt
```

Figure 11

AAAGgtatgttctttgaataccttacttataatgctcatgctaaaat ————— cf11

Figure 14

SEQUENCE LISTING

<160> NUMBER OF SEQ ID NOS: 73

<210> SEQ ID NO 1
<211> LENGTH: 10
<212> TYPE: RNA
<213> ORGANISM: artificial sequence
<220> FEATURE:
<223> OTHER INFORMATION: coagulation Factor IX_SH1

<400> SEQUENCE: 1
agauuaugac        10

<210> SEQ ID NO 2
<211> LENGTH: 11
<212> TYPE: RNA
<213> ORGANISM: artificial sequence
<220> FEATURE:
<223> OTHER INFORMATION: coagulation Factor IX_SH7

<400> SEQUENCE: 2
ucuuauucag a        11

<210> SEQ ID NO 3
<211> LENGTH: 13
<212> TYPE: RNA
<213> ORGANISM: artificial sequence
<220> FEATURE:
<223> OTHER INFORMATION: cystic fibrosis_SH1

<400> SEQUENCE: 3
ucaaagaaca uac        13

<210> SEQ ID NO 4
<211> LENGTH: 16
<212> TYPE: RNA
<213> ORGANISM: artificial sequence
<220> FEATURE:
<223> OTHER INFORMATION: cystic fibrosis_SH11

<400> SEQUENCE: 4
auaaguaagg uauuca        16

<210> SEQ ID NO 5
<211> LENGTH: 592
<212> TYPE: DNA
<213> ORGANISM: Homo sapiens

<400> SEQUENCE: 5
taaggaccag cttctttggg agagaacaga cgcaggggcg ggagggaaaa agggagaggc        60
agacgtcact tccccttggc ggctctggca gcagattggt cggttgagtg gcagaaaggc       120
agacggggac tgggcaaggc actgtcggtg acatcacgga cagggcgact tctatgtaga       180
tgaggcagcg cagaggctga cgtcttcgcc acttgctgct tcaccacgaa ggagttcccg       240
tgccctggga gcgggttcag gaccgctgat cggaagtgag aatcccagct gtgtgtcagg       300
gctggaaagg gctcgggagt gcgcggggca agtgaccgtg tgtgtaaaga gtgaggcgta       360
tgaggctgtg tcggggcaga ggcccaagat ctgatactta cctggcaggg gagataccat       420
gatcacgaag gtggttttcc cagggcgagg cttatccatt gcactccgga tgtgctgacc       480
cctgcgattt ccccaaatgt gggaaactcg actgcataat tgtggtagt ggggactgc        540 gttcgcgctt tccctgact ttctggagtt tcaaaagtag actgtacgct aa       592

```
<210> SEQ ID NO 6
<211> LENGTH: 33
<212> TYPE: DNA
<213> ORGANISM: artificial sequence
<220> FEATURE:
<223> OTHER INFORMATION: coagulation Factor IX U1 exon 5 C3T5A6 direct

<400> SEQUENCE: 6
gatctcatta tgacctggca ggggagatac cat                                33

<210> SEQ ID NO 7
<211> LENGTH: 33
<212> TYPE: DNA
<213> ORGANISM: artificial sequence
<220> FEATURE:
<223> OTHER INFORMATION: coagulation Factor IX U1 exon 5 C3T5A6 reverse

<400> SEQUENCE: 7
gatcatggta tctcccctgc caggtcataa tga                                33

<210> SEQ ID NO 8
<211> LENGTH: 36
<212> TYPE: DNA
<213> ORGANISM: artificial sequence
<220> FEATURE:
<223> OTHER INFORMATION: U1 coagulation Factor IX exon 5 SH-7 direct

<400> SEQUENCE: 8
gatctcatat gacctgctgg gcaggggaga taccat                             36

<210> SEQ ID NO 9
<211> LENGTH: 36
<212> TYPE: DNA
<213> ORGANISM: artificial sequence
<220> FEATURE:
<223> OTHER INFORMATION: U1 coagulation Factor IX exon 5 SH-7 reverse

<400> SEQUENCE: 9
gatcatggta tctcccctgc ccagcaggtc atatga                             36

<210> SEQ ID NO 10
<211> LENGTH: 34
<212> TYPE: DNA
<213> ORGANISM: artificial sequence
<220> FEATURE:
<223> OTHER INFORMATION: U1 coagulation Factor IX exon 5 SH1 direct

<400> SEQUENCE: 10
gatctcatag attatgacgc agggagata ccat                                34

<210> SEQ ID NO 11
<211> LENGTH: 34
<212> TYPE: DNA
<213> ORGANISM: artificial sequence
<220> FEATURE:
<223> OTHER INFORMATION: U1 coagulation Factor IX exon 5 SH1 reverse

<400> SEQUENCE: 11
gatcatggta tctcccctgc gtcataatct atga                               34

<210> SEQ ID NO 12
<211> LENGTH: 35
<212> TYPE: DNA
<213> ORGANISM: artificial sequence
<220> FEATURE:
<223> OTHER INFORMATION: U1 coagulation Factor IX exon 5 SH7 direct
```

-continued

<400> SEQUENCE: 12
gatctcatct tattcagatg caggggagat accat                35

<210> SEQ ID NO 13
<211> LENGTH: 35
<212> TYPE: DNA
<213> ORGANISM: artificial sequence
<220> FEATURE:
<223> OTHER INFORMATION: U1 coagulation Factor IX exon 5 SH7 reverse

<400> SEQUENCE: 13
gatcatggta tctcccctgc atctgaataa gatga                35

<210> SEQ ID NO 14
<211> LENGTH: 34
<212> TYPE: DNA
<213> ORGANISM: artificial sequence
<220> FEATURE:
<223> OTHER INFORMATION: U1 coagulation Factor IX exon 5 SH9 direct

<400> SEQUENCE: 14
gatctcattc ttattcaggc agggagata ccat                34

<210> SEQ ID NO 15
<211> LENGTH: 34
<212> TYPE: DNA
<213> ORGANISM: artificial sequence
<220> FEATURE:
<223> OTHER INFORMATION: U1 coagulation Factor IX exon 5 SH9 reverse

<400> SEQUENCE: 15
gatcatggta tctcccctgc ctgaataaga atga                34

<210> SEQ ID NO 16
<211> LENGTH: 34
<212> TYPE: DNA
<213> ORGANISM: artificial sequence
<220> FEATURE:
<223> OTHER INFORMATION: U1 coagulation Factor IX exon 5 SH10 direct

<400> SEQUENCE: 16
gatctcatat cttattcagc agggagata ccat                34

<210> SEQ ID NO 17
<211> LENGTH: 34
<212> TYPE: DNA
<213> ORGANISM: artificial sequence
<220> FEATURE:
<223> OTHER INFORMATION: U1 coagulation Factor IX exon 5 SH10 reverse

<400> SEQUENCE: 17
gatcatggta tctcccctgc tgaataagat atga                34

<210> SEQ ID NO 18
<211> LENGTH: 34
<212> TYPE: DNA
<213> ORGANISM: artificial sequence
<220> FEATURE:
<223> OTHER INFORMATION: U1 coagulation Factor IX exon 5 SH13 direct

<400> SEQUENCE: 18
gatctcataa aatcttatgc agggagata ccat                34

<210> SEQ ID NO 19
<211> LENGTH: 34

```
<212> TYPE: DNA
<213> ORGANISM: artificial sequence
<220> FEATURE:
<223> OTHER INFORMATION: U1 coagulation Factor IX exon 5 SH13 reverse

<400> SEQUENCE: 19
gatcatggta tctcccctgc ataagatttt atga                                34

<210> SEQ ID NO 20
<211> LENGTH: 35
<212> TYPE: DNA
<213> ORGANISM: artificial sequence
<220> FEATURE:
<223> OTHER INFORMATION: U1 coagulation Factor IX exon 5 SH16 direct

<400> SEQUENCE: 20
gatctcatat aaaaaatctg caggggagat accat                               35

<210> SEQ ID NO 21
<211> LENGTH: 35
<212> TYPE: DNA
<213> ORGANISM: artificial sequence
<220> FEATURE:
<223> OTHER INFORMATION: U1 coagulation Factor IX exon 5 SH16 reverse

<400> SEQUENCE: 21
gatcatggta tctcccctgc agatttttta tatga                               35

<210> SEQ ID NO 22
<211> LENGTH: 35
<212> TYPE: DNA
<213> ORGANISM: artificial sequence
<220> FEATURE:
<223> OTHER INFORMATION: U1 coagulation Factor IX exon 5 SH22 direct

<400> SEQUENCE: 22
gatctcatat ttctttaaag caggggagat accat                               35

<210> SEQ ID NO 23
<211> LENGTH: 35
<212> TYPE: DNA
<213> ORGANISM: artificial sequence
<220> FEATURE:
<223> OTHER INFORMATION: U1 coagulation Factor IX exon 5 SH22 reverse

<400> SEQUENCE: 23
gatcatggta tctcccctgc tttaaagaaa tatga                               35

<210> SEQ ID NO 24
<211> LENGTH: 35
<212> TYPE: DNA
<213> ORGANISM: artificial sequence
<220> FEATURE:
<223> OTHER INFORMATION: U1 coagulation Factor IX exon 5 SH33 direct

<400> SEQUENCE: 24
gatctcattc agatacagag caggggagat accat                               35

<210> SEQ ID NO 25
<211> LENGTH: 35
<212> TYPE: DNA
<213> ORGANISM: artificial sequence
<220> FEATURE:
<223> OTHER INFORMATION: U1 coagulation Factor IX exon 5 SH33 reverse

<400> SEQUENCE: 25
```

-continued gatcatggta tctcccctgc tctgtatctg aatga					35

<210> SEQ ID NO 26
<211> LENGTH: 34
<212> TYPE: DNA
<213> ORGANISM: artificial sequence
<220> FEATURE:
<223> OTHER INFORMATION: U1 coagulation Factor IX exon 5 SH38 direct

<400> SEQUENCE: 26
gatctcatag tttcagatgc agggagata ccat					34

<210> SEQ ID NO 27
<211> LENGTH: 34
<212> TYPE: DNA
<213> ORGANISM: artificial sequence
<220> FEATURE:
<223> OTHER INFORMATION: U1 coagulation Factor IX exon 5 SH38 reverse

<400> SEQUENCE: 27
gatcatggta tctcccctgc atctgaaact atga					34

<210> SEQ ID NO 28
<211> LENGTH: 34
<212> TYPE: DNA
<213> ORGANISM: artificial sequence
<220> FEATURE:
<223> OTHER INFORMATION: U1 coagulation Factor IX exon 5 SH63 direct

<400> SEQUENCE: 28
gatctcattt atgtaggtgc agggagata ccat					34

<210> SEQ ID NO 29
<211> LENGTH: 34
<212> TYPE: DNA
<213> ORGANISM: artificial sequence
<220> FEATURE:
<223> OTHER INFORMATION: U1 coagulation Factor IX exon 5 SH63 reverse

<400> SEQUENCE: 29
gatcatggta tctcccctgc acctacataa atga					34

<210> SEQ ID NO 30
<211> LENGTH: 34
<212> TYPE: DNA
<213> ORGANISM: artificial sequence
<220> FEATURE:
<223> OTHER INFORMATION: U1 exon 7 survival of motor neuron-1G-2G-3A
      reverse

<400> SEQUENCE: 30
gatcatggta tctcccctgc ggagtaagtt atga					34

<210> SEQ ID NO 31
<211> LENGTH: 34
<212> TYPE: DNA
<213> ORGANISM: artificial sequence
<220> FEATURE:
<223> OTHER INFORMATION: U1 exon 7 survival of motor neuron-1G-2G-3A
      direct

<400> SEQUENCE: 31
gatctcataa cttactccgc agggagata ccat					34

<210> SEQ ID NO 32
<211> LENGTH: 34

```
<212> TYPE: DNA
<213> ORGANISM: artificial sequence
<220> FEATURE:
<223> OTHER INFORMATION: U1 exon 7 survival of motor neuron sh2 reverse

<400> SEQUENCE: 32
gatcatggta tctcccctgc taagtctgct atga                            34

<210> SEQ ID NO 33
<211> LENGTH: 34
<212> TYPE: DNA
<213> ORGANISM: artificial sequence
<220> FEATURE:
<223> OTHER INFORMATION: U1 exon 7 survival of motor neuron sh2 direct

<400> SEQUENCE: 33
gatctcatag cagacttagc aggggagata ccat                            34

<210> SEQ ID NO 34
<211> LENGTH: 34
<212> TYPE: DNA
<213> ORGANISM: artificial sequence
<220> FEATURE:
<223> OTHER INFORMATION: U1 exon 7 survival of motor neuron sh17 reverse

<400> SEQUENCE: 34
gatcatggta tctcccctgc tatgaaagtt atga                            34

<210> SEQ ID NO 35
<211> LENGTH: 34
<212> TYPE: DNA
<213> ORGANISM: artificial sequence
<220> FEATURE:
<223> OTHER INFORMATION: U1 exon 7 survival of motor neuron sh17 direct

<400> SEQUENCE: 35
gatctcataa ctttcatagc aggggagata ccat                            34

<210> SEQ ID NO 36
<211> LENGTH: 33
<212> TYPE: DNA
<213> ORGANISM: artificial sequence
<220> FEATURE:
<223> OTHER INFORMATION: U1 cystic fibrosis transmembrane conductance
      regulator exon 12-1A 4T direct

<400> SEQUENCE: 36
gatctcatac atacttggca ggggagatac cat                             33

<210> SEQ ID NO 37
<211> LENGTH: 33
<212> TYPE: DNA
<213> ORGANISM: artificial sequence
<220> FEATURE:
<223> OTHER INFORMATION: U1 cystic fibrosis transmembrane conductance
      regulator exon 12-1A 4T reverse

<400> SEQUENCE: 37
gatcatggta tctcccctgc caagtatgta tga                             33

<210> SEQ ID NO 38
<211> LENGTH: 33
<212> TYPE: DNA
<213> ORGANISM: artificial sequence
<220> FEATURE:
<223> OTHER INFORMATION: U1 cystic fibrosis transmembrane conductance
      regulator exon 12 G3 T4 direct
```

<400> SEQUENCE: 38
gatctcatac acacctggca ggggagatac cat				33

<210> SEQ ID NO 39
<211> LENGTH: 33
<212> TYPE: DNA
<213> ORGANISM: artificial sequence
<220> FEATURE:
<223> OTHER INFORMATION: U1 cystic fibrosis transmembrane conductance
      regulator exon 12 G3 T4 reverse

<400> SEQUENCE: 39
gatcatggta tctcccctgc caggtgtgta tga				33

<210> SEQ ID NO 40
<211> LENGTH: 33
<212> TYPE: DNA
<213> ORGANISM: artificial sequence
<220> FEATURE:
<223> OTHER INFORMATION: U1 cystic fibrosis transmembrane conductance
      regulator exon 12 T4 A5 direct

<400> SEQUENCE: 40
gatctcatat atacctggca ggggagatac cat				33

<210> SEQ ID NO 41
<211> LENGTH: 33
<212> TYPE: DNA
<213> ORGANISM: artificial sequence
<220> FEATURE:
<223> OTHER INFORMATION: U1 cystic fibrosis transmembrane conductance
      regulator exon 12 T4 A5 reverse

<400> SEQUENCE: 41
gatcatggta tctcccctgc caggtatata tga				33

<210> SEQ ID NO 42
<211> LENGTH: 35
<212> TYPE: DNA
<213> ORGANISM: artificial sequence
<220> FEATURE:
<223> OTHER INFORMATION: U1 cystic fibrosis sh+1 direct

<400> SEQUENCE: 42
gatctctcaa agaacatacg caggggagat accat				35

<210> SEQ ID NO 43
<211> LENGTH: 35
<212> TYPE: DNA
<213> ORGANISM: artificial sequence
<220> FEATURE:
<223> OTHER INFORMATION: U1 cystic fibrosis sh+1 reverse

<400> SEQUENCE: 43
gatcatggta tctcccctgc gtatgttctt tgaga				35

<210> SEQ ID NO 44
<211> LENGTH: 35
<212> TYPE: DNA
<213> ORGANISM: artificial sequence
<220> FEATURE:
<223> OTHER INFORMATION: cystic fibrosis 12 SH+9 direct

<400> SEQUENCE: 44
gatctcatag gtattcaaag caggggagat accat				35

<210> SEQ ID NO 45
<211> LENGTH: 35
<212> TYPE: DNA
<213> ORGANISM: artificial sequence
<220> FEATURE:
<223> OTHER INFORMATION: cystic fibrosis 12 SH+9 reverse

<400> SEQUENCE: 45
gatcatggta tctcccctgc tttgaatacc tatga          35

<210> SEQ ID NO 46
<211> LENGTH: 38
<212> TYPE: DNA
<213> ORGANISM: artificial sequence
<220> FEATURE:
<223> OTHER INFORMATION: cystic fibrosis 12 SH+11 direct

<400> SEQUENCE: 46
gatctcataa gtaaggtatt cagcagggga gataccat          38

<210> SEQ ID NO 47
<211> LENGTH: 38
<212> TYPE: DNA
<213> ORGANISM: artificial sequence
<220> FEATURE:
<223> OTHER INFORMATION: cystic fibrosis 12 SH+11 reverse

<400> SEQUENCE: 47
gatcatggta tctcccctgc tgaataccttacttatga          38

<210> SEQ ID NO 48
<211> LENGTH: 35
<212> TYPE: DNA
<213> ORGANISM: artificial sequence
<220> FEATURE:
<223> OTHER INFORMATION: cystic fibrosis 12 SH+33 direct

<400> SEQUENCE: 48
gatcatggta tctcccctgc tcatgctaaa ataga          35

<210> SEQ ID NO 49
<211> LENGTH: 35
<212> TYPE: DNA
<213> ORGANISM: artificial sequence
<220> FEATURE:
<223> OTHER INFORMATION: cystic fibrosis 12 SH+33 reverse

<400> SEQUENCE: 49
gatctctatt ttagcatgag caggggagat accat          35

<210> SEQ ID NO 50
<211> LENGTH: 11
<212> TYPE: RNA
<213> ORGANISM: artificial sequence
<220> FEATURE:
<223> OTHER INFORMATION: coagulation Factor IX_SH-7

<400> SEQUENCE: 50
ugaccugcug g          11

<210> SEQ ID NO 51
<211> LENGTH: 9
<212> TYPE: RNA
<213> ORGANISM: artificial sequence
<220> FEATURE:

```
<223> OTHER INFORMATION: coagulation Factor IX_SH9

<400> SEQUENCE: 51 ucuuauuca                                                                    9

<210> SEQ ID NO 52
<211> LENGTH: 9
<212> TYPE: RNA
<213> ORGANISM: artificial sequence
<220> FEATURE:
<223> OTHER INFORMATION: coagulation Factor IX_SH10

<400> SEQUENCE: 52 aucuuauuc                                                                    9

<210> SEQ ID NO 53
<211> LENGTH: 9
<212> TYPE: RNA
<213> ORGANISM: artificial sequence
<220> FEATURE:
<223> OTHER INFORMATION: coagulation Factor IX_SH13

<400> SEQUENCE: 53 aaaaucuua                                                                    9

<210> SEQ ID NO 54
<211> LENGTH: 9
<212> TYPE: RNA
<213> ORGANISM: artificial sequence
<220> FEATURE:
<223> OTHER INFORMATION: coagulation Factor IX_SH16

<400> SEQUENCE: 54 uaaaaaauc                                                                    9

<210> SEQ ID NO 55
<211> LENGTH: 9
<212> TYPE: RNA
<213> ORGANISM: artificial sequence
<220> FEATURE:
<223> OTHER INFORMATION: coagulation Factor IX_SH22

<400> SEQUENCE: 55 uuucuuuaa                                                                    9

<210> SEQ ID NO 56
<211> LENGTH: 9
<212> TYPE: RNA
<213> ORGANISM: artificial sequence
<220> FEATURE:
<223> OTHER INFORMATION: Spinal muscular atrophy_SH2

<400> SEQUENCE: 56 gcagacuua                                                                    9

<210> SEQ ID NO 57
<211> LENGTH: 9
<212> TYPE: RNA
<213> ORGANISM: artificial sequence
<220> FEATURE:
<223> OTHER INFORMATION: Spinal muscular atrophy_SH17

<400> SEQUENCE: 57 acuuucaua                                                                    9
```

-continued

```
<210> SEQ ID NO 58
<211> LENGTH: 9
<212> TYPE: RNA
<213> ORGANISM: artificial sequence
<220> FEATURE:
<223> OTHER INFORMATION: C3T5A6

<400> SEQUENCE: 58 uaugaccug                                                              9

<210> SEQ ID NO 59
<211> LENGTH: 9
<212> TYPE: RNA
<213> ORGANISM: artificial sequence
<220> FEATURE:
<223> OTHER INFORMATION: -1G-2G-3A

<400> SEQUENCE: 59 acuuacucc                                                              9

<210> SEQ ID NO 60
<211> LENGTH: 9
<212> TYPE: RNA
<213> ORGANISM: artificial sequence
<220> FEATURE:
<223> OTHER INFORMATION: -1A+4T

<400> SEQUENCE: 60 acauacuug                                                              9

<210> SEQ ID NO 61
<211> LENGTH: 9
<212> TYPE: RNA
<213> ORGANISM: artificial sequence
<220> FEATURE:
<223> OTHER INFORMATION: +3G+4T

<400> SEQUENCE: 61 acacaccug                                                              9

<210> SEQ ID NO 62
<211> LENGTH: 9
<212> TYPE: RNA
<213> ORGANISM: artificial sequence
<220> FEATURE:
<223> OTHER INFORMATION: +4T+5A

<400> SEQUENCE: 62 auauaccug                                                              9

<210> SEQ ID NO 63
<211> LENGTH: 12
<212> TYPE: RNA
<213> ORGANISM: artificial sequence
<220> FEATURE:
<223> OTHER INFORMATION: Capable of recognizing the splicing donor site.

<400> SEQUENCE: 63
auacuuaccu gg                                                         12

<210> SEQ ID NO 64
<211> LENGTH: 15
<212> TYPE: DNA
<213> ORGANISM: artificial sequence
<220> FEATURE:
<223> OTHER INFORMATION: Oligonucleotide specific for generating
      modified U1snRNAs when used to replace sequences encoding the
```

U1snRNA single stranded tail region.
<220> FEATURE:
<221> NAME/KEY: misc_feature
<222> LOCATION: (3)..(4)
<223> OTHER INFORMATION: k is g or t

<400> SEQUENCE: 64
tgckkctttt agatg                                              15

<210> SEQ ID NO 65
<211> LENGTH: 13
<212> TYPE: DNA
<213> ORGANISM: artificial sequence
<220> FEATURE:
<223> OTHER INFORMATION: Oligonucleotide specific for generating
      modified U1snRNAswhen used to replace sequences encoding the
      U1snRNA single stranded tail region.
<220> FEATURE:
<221> NAME/KEY: misc_feature
<222> LOCATION: (2)..(2)
<223> OTHER INFORMATION: n is a, c, g, or t

<400> SEQUENCE: 65
cnggtcataa tct                                                13

<210> SEQ ID NO 66
<211> LENGTH: 77
<212> TYPE: DNA
<213> ORGANISM: artificial sequence
<220> FEATURE:
<223> OTHER INFORMATION: Modified U1snRNA employed for the correction
      of exon 5 splicing defects of the clotting factor IX gene.

<400> SEQUENCE: 66
ccagcaggtc ataatctgaa taagattttt taaagaaaat ctgtatctga aacttcagca    60
ttttaacaaa cctacat                                                  77

<210> SEQ ID NO 67
<211> LENGTH: 44
<212> TYPE: DNA
<213> ORGANISM: artificial sequence
<220> FEATURE:
<223> OTHER INFORMATION: Modified SMN U1 snRNAs employed for correcting
      the splicing defect of the SMN2 gene.

<400> SEQUENCE: 67
taaggagtaa gtctgccagc attatgaaag tgaatcttac tttt                    44

<210> SEQ ID NO 68
<211> LENGTH: 47
<212> TYPE: DNA
<213> ORGANISM: artificial sequence
<220> FEATURE:
<223> OTHER INFORMATION: Shows the localization of the ExSpeU1 ef11 for
      correcting the splicing defects of exon 12 of the CFTR gene

<400> SEQUENCE: 68
aaaggtatgt tctttgaata ccttacttat aatgctcatg ctaaaat                 47

<210> SEQ ID NO 69
<211> LENGTH: 15
<212> TYPE: DNA
<213> ORGANISM: artificial sequence
<220> FEATURE:
<223> OTHER INFORMATION: Sequence of acceptor/donor site

<400> SEQUENCE: 69

```
tgctgctttt agatg                                                    15

<210> SEQ ID NO 70
<211> LENGTH: 15
<212> TYPE: DNA
<213> ORGANISM: artificial sequence
<220> FEATURE:
<223> OTHER INFORMATION: Sequence of acceptor/donor site

<400> SEQUENCE: 70
tgcgtctttt agatg                                                    15

<210> SEQ ID NO 71
<211> LENGTH: 13
<212> TYPE: RNA
<213> ORGANISM: artificial sequence
<220> FEATURE:
<223> OTHER INFORMATION: FIX33 Binding Sequence

<400> SEQUENCE: 71
auucagauac aga                                                      13

<210> SEQ ID NO 72
<211> LENGTH: 12
<212> TYPE: RNA
<213> ORGANISM: artificial sequence
<220> FEATURE:
<223> OTHER INFORMATION: FIX38 Binding Sequence

<400> SEQUENCE: 72
auaguuucag au                                                       12

<210> SEQ ID NO 73
<211> LENGTH: 12
<212> TYPE: RNA
<213> ORGANISM: artificial sequence
<220> FEATURE:
<223> OTHER INFORMATION: FIX63 Binding Sequence

<400> SEQUENCE: 73
auuuauguag gu                                                       12
```

MODIFIED HUMAN U1SNRNA MOLECULE, A GENE ENCODING FOR THE MODIFIED HUMAN U1SNRNA MOLECULE, AN EXPRESSION VECTOR INCLUDING THE GENE, AND THE USE THEREOF IN GENE THERAPY

CROSS-REFERENCE TO RELATED APPLICATIONS

This application is a U.S. national stage of PCT/IB2011/054573 filed on Oct. 14, 2011 which claims priority to and the benefit of Italian Application No. TO2010A000840 filed on Oct. 15, 2010, the contents of which are incorporated herein by reference.

FIELD OF THE INVENTION

The present invention concerns modified human snRNA molecules (hereinafter designated as Exon Specific U1—ExSpeU1), which are suitable to be used in gene therapy methods. In particular, the invention relates to snRNA molecules capable of correcting aberrant splicing processes caused by genetic mutations and related to human diseases with different case histories, which are often very serious.

BACKGROUND OF THE INVENTION

Many human genetic diseases (about 15%) are caused by genetic mutations that, by interfering with the correct messenger RNA intracellular maturation, compromise the accurate subsequent protein biosynthesis and induce synthesis of non-functional proteins. Mostly, the point mutations accountable for splicing defects concern gene sequences that are critical for the recognition of the primary transcript by the machinery appointed for processing the same. The donor and acceptor sites located at the exon-intron boundaries, as well as gene-specific regulatory elements in exons or introns (Cartegni L et al., 2002; Pagani et al., 2004) are among the most significant sequences. As a consequence of these mutations, various molecular events, which most frequently concern the exclusion of one exon from the mature transcript, the so-called exon skipping, may be induced.

It has been known for a long time that molecular changes in the processing of messenger RNA, which involve for instance exon skipping, represent the main etiopathogenic mechanism of various human diseases, among which hemophilia B, cystic fibrosis, and spinal muscular atrophy, which share the seriousness of their clinical courses. Different types of mutations can induce exon skipping, and specifically mutations in the donor site (or 5' splicing site), mutations in the acceptor site (3' splicing site), or exonic mutations. As examples of different types of mutations that induce exon skipping, following are described three models of human diseases.

The defect in the coagulation factor IX (FIX) accounts for the onset of hemophilia B, a disease accompanied by varying degrees of hemorrhagic manifestations, sometimes very serious and disabling. In some cases, the disease is caused by splicing defects. In particular, the exclusion of exon 5 from mRNA during the splicing process is caused both by mutations at position −2 within the exon 5 donor site of the factor IXgene (F9), and by mutations at positions −8 and −9 within the poly-pyrimidine sequence in the acceptor site.

The limitations of the current hemophilia B therapy, which is mainly based on the frequent infusion of recombinant exogenous FIX or of FIX directly derived from plasma, emphasize the need of developing alternative approaches that are characterized by a greater efficacy and a long-lasting effect.

Cystic fibrosis (CF) is the most frequent lethal congenital hereditary disease in the Caucasian population: one newborn out of 2500-2700 born-alive infants is affected by it.

The pathogenesis of this disease is secondary to an anomaly of a protein designated as CFTR (Cystic Fibrosis Transmembrane Conductance Regulator) localized in the apical membrane of epithelium cells and having the function of regulating the hydroelectrolytic exchanges.

As a consequence of CFTR modification, the transfer of salts through cell membranes is compromised, mainly causing a production of secretions that could be defined as "dehydrated": a sweat very rich in sodium and chlorine and a dense and viscous mucus that tends to obstruct the ducts, compromising the function of various organs and systems. In the course of several studies, many modifications in the CFTR gene sequence were identified as associated with cystic fibrosis, which induce exon skipping. In particular, skipping of exon 12 is caused both by mutations localized within the splicing donor site of the exon itself, and by exonic mutations.

Spinal muscular atrophy (SMA, OMIM 253300, 253550, and 253400) is a recessive autosomal neuromuscular disease characterized by degeneration of spinal marrow alpha motoneurons, with an estimated prevalence of 1/10,000 born. SMA is associated with clinical syndromes that range from extremely serious, with critical muscle hypotonia and weakness since birth, to milder forms in which the onset occurs later during childhood or adolescence. To date, no treatment for this disease, which generally leads to death at an age that depends on the seriousness of the case history, has yet been identified.

In 95% of cases, the disease is caused by absence of the SMN1 gene. In the human genome, there is a gene homologous to SMN1 called SMN2. However, expression of SMN2 is impaired by a synonymous mutation in the exon which results in an aberrant maturation of the messenger RNA with consequent skipping of exon 7 and inactivation of the gene itself. Approaches designed to increase the number of exon 7-containing SMN2 transcripts would therefore allow to apply a compensation therapy for the absence of the SMN1 gene thanks to the correct expression of SMN2, with considerable implications for a potential effective treatment for SMA.

During the splicing process, the small nuclear RNAs (snRNAs) play a primary role as essential components of the spliceosome, the cell machinery appointed to mediate the entire mRNA maturation process. In particular, the small U1 RNA (U1snRNA), 164 ribonucleotides in length, is encoded by genes that occur in several copies within the human genome and represents the ribonucleic component of the nuclear particle U1snRNP. The U1snRNA molecules have a stem and loop tridimensional structure and within the 5' region they include a single-stranded sequence, generally 9 nucleotides in length, capable of binding by complementary base pairing the splicing donor site on the pre-mRNA molecule (Horowitz et al., 1994). FIG. 1 shows a schematic representation of the wild-type U1snRNA structure. The sequence in the 5' region capable of recognizing the splicing donor site is shown paired with the consensus sequence of the splicing donor site in the primary transcripts of eukaryotic genes. Such a sequence exhibits varying degrees of conservation and is located at the exon/intron junction. The recognition mediated by the U1snRNA 5' region is critical for defining the exon/intron junctions on the primary transcript and for a correct assembly of the spliceosome complex.

The increasing number of human genetic diseases associated with pre-mRNA splicing defects, and the frequent seriousness of the clinical course of the same, stimulated in the last few years the research for therapeutic molecules aimed at correcting splicing defects at the molecular level.

The use of modified U1snRNA molecules capable of inducing in vitro the correct inclusion of the exon and restoring the correct splicing of coagulation factor VII mRNA in case of mutations located at the 5'ss site is described in Pinotti M et al. 2008 and Pinotti M et al., 2009. The illustrated mechanism is based on the recognition and binding of the modified U1snRNA directly onto the 5' mutated splicing site. However, this method presents a certain degree of non-specificity of action of the therapeutic snRNA molecule towards the target gene, due to the relative conservation of the 5' ss sites and consequent risk of interfering with the maturation of transcripts generated from other functional wild-type genes. Moreover, it requires the use of a U1snRNA modified for each mutation in the 5' ss.

SUMMARY OF THE INVENTION

The present invention demonstrates that modified U1 snRNA molecules complementary to intron sequences downstream of the 5' splicing site (and herein defined as Exon Specific U1s, ExSpeU1), are capable of restoring, during the splicing process, the exon inclusion which was impaired by different types of mutations. In three different human genetic disease models of therapeutic interest (spinal muscular atrophy, hemophilia, and cystic fibrosis), the present invention demonstrates that, a single ExSpeU1 or a group of ExSpeU1s are able to induce the inclusion of the corresponding exon for each disease model. A single ExSpeU1 or a group of ExSpeU1s correct the exon skipping caused by mutations in the donor site, mutations in the poly-pyrimidine tract of the acceptor site, and mutations in regulatory exon sequences. The correction effectiveness obtained with the ExSpeU1s is the same as that described in the prior art, but it would guarantee a greater selectivity of action on the target gene transcript of therapeutic interest. The ExSpeU1 approach allows to use a single modified U1-snRNA for correcting a panel of different genetic mutations that cause exon skipping.

These and other objects are achieved by a modified human U1snRNA molecule as defined in claim 1. The modified human U1snRNA molecule is characterized in that a portion of the single-stranded nucleotide sequence in the 5' region of the wild-type human U1snRNA is replaced by a binding single-stranded nucleotide sequence capable of hybridizing to a target nucleotide sequence on the primary transcript of a target gene of therapeutic interest bearing a mutation which induces aberrant splicing. The target nucleotide sequence of the U1snRNA molecule is located in a region of the pre-mRNA comprised between 2 and 50 base pairs downstream of an exon/intron junction site (5' ss), provided that the target nucleotide sequence does not comprise said exon/intron junction site. Preferably, the target nucleotide sequence is 5 to 50 nucleotides in length, more preferably 9 to 30 nucleotides.

Compared to the prior art, the U1snRNA molecules subject of the invention have the advantage of performing a targeted and selective (exon-specific) action, as they bind target nucleotide sequences on the primary transcript localized within the intron regions flanking the splicing donor site, which exhibit a lower degree of conservation compared to the sequences of the exon/intron junction sites. It is however surprising that, though operating on target sequences that do not include the exon/intron junction site, the U1snRNA molecules of the invention are all the same capable of inducing inclusion of the exon in the presence of different types of mutations, including the exonic ones or those on the acceptor site. Further features of the invention are defined in the appended claims, which are an integral part of the technical teachings of the present specification.

BRIEF DESCRIPTION OF THE DRAWINGS

FIG. 5 illustrates localization of the binding sites on the modified U1snRNA employed for the correction of exon 5 splicing defects of the clotting factor IXgene. The sequence of exon 5 is indicated in capital letters, whereas the remaining sequence indicates the intron (SEQ ID NO: 66).

FIG. 11 illustrates the localization of the modified SMN U1 snRNAs employed for correcting the splicing defect of the SMN2 gene (SEQ ID NO: 67).

FIG. 14 schematically illustrates the localization of the ExSpeU1 ef11 that was used for correcting the splicing defects of exon 12 of the CFTR gene (SEQ ID NO: 68).

DETAILED DESCRIPTION OF THE INVENTION

Figure 1:
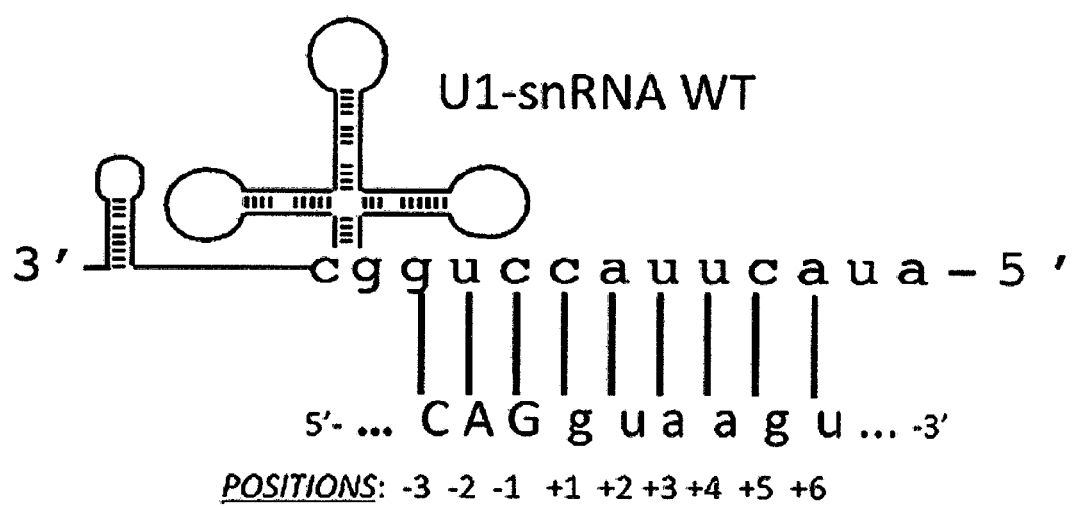
FIG. 1 illustrates a schematic representation of the wild-type U1snRNA structure. The sequence in the 5' region capable of recognizing the splicing donor site (SEQ ID NO: 63) is shown paired with the consensus sequence of the splicing donor site in the primary transcripts of eukaryotic genes.

In a preferred embodiment, the portion of the single-stranded 5' region of the wild-type U1snRNA which is replaced by the binding nucleotide sequence is from 9 to 12 nucleotides in length.

Preferably, the mutations that are corrected by the ExSpeU1s and cause exon skipping are located in the sequence comprised between 3 and 50 base pairs upstream of an intron/exon junction site (3' splice site), exonic mutations and mutations within the consensus sequence of the splicing donor site.

The coagulation factor IX, the SMN2, and the CFTR genes are mentioned by way of example among the genes of therapeutic interest, that is those bearing mutations related to diseases that lend themselves to treatment with the ExSpeU1 s of the present invention.

In a preferred embodiment, the modified human U1snRNA molecule of the invention includes a binding nucleotide sequence selected from the group consisting of SEQ ID NO: 1 to 4 and 51 to 57, more preferably from 1 to 3 and 51 to 57.

In a preferred embodiment, the gene comprises a promoter sequence and a polyadenylation signal sequence. The inventors verified that the endogenous promoter of the gene encoding for human U1snRNA is particularly suitable, although other per se known promoters can also be used, which may easily be selected by a person of ordinary skill in the art.

The sequence of the forward strand of the wild-type human U1snRNA encoding gene (designated as SEQ ID NO: 5 in the sequence listing) is reported hereinafter by way of example, wherein the portion of the single-stranded 5' region which in the modified U1snRNA molecule is replaced by the binding sequence is in bold. The sequences of the unique BglII and BclI restriction sites, used for inserting the binding sequences, are underlined. In addition to the RNA encoding region, which is shown in capital letters, the SEQ ID NO: 5 gene sequence also comprises some regulatory elements required for its expression, such as the promoter and the polyadenylation signal.

(SEQ ID NO: 5)
5'-taaggaccagcttctttgggagagaacagacgcagggcgggaggga aaaagggagaggcagacgtcacttcccttggcggctctggcagcagatt ggtcggttgagtggcagaaaggcagacggggactgggcaaggcactgtcg gtgacatcacggacagggcgacttctatgtagatgaggcagcgcagaggc tgacgtcttcgccacttgctgcttcaccacgaaggagttcccgtgccctg ggagcgggttcaggaccgctgatcggaagtgagaatcccagctgtgtgtc agggctggaaagggctcgggagtgcgcggggcaagtgaccgtgtgtgtaa agagtgaggcgtatgaggctgtgtcggggcagaggcccaagatctgATAC

TTACCTGGCAGGGGAGATACCATGATCACGAAGGTGGTTTTCCCAGGGCG

AGGCTTATCCATTGCACTCCGGATGTGCTGACCCCTGCGATTTATGTGGG

AAACTCGACTGCATACCCCAAATTTGTGGTAGTGGGGGACTGCGTTCGCG

CTTTCCCCTGactttctggagtttcaaaagtagactgtacgctaa-3'.

Obviously, the above gene sequence is provided solely by way of example. Alternatively, in order to construct the gene encoding for the modified U1snRNAs of the invention, any gene sequence homologous to SEQ ID NO: 5 can be used, that is one able to encode for a U1snRNA capable of effectively mediating the recognition of the splicing donor site.

The preparation method for the different modified U1snRNA molecules subject of the invention, which contain the different binding sequences, is described in detail in the section of the Examples.

Still another object of the invention is an expression vector comprising an isolated gene as defined previously. The mostly preferred expression vector is an adeno-associated viral vector, although other types of expression vectors, which are per se known to a person of ordinary skill in the art, may also be used.

As previously described, the modified human U1snRNA molecule, the gene encoding for such an RNA molecule, and the vector including said gene are suitable to be used for the therapeutic treatment of a genetic disease caused by or associated with an aberrant splicing and characterized by exon skipping. Preferably, but not by way of limitation, the disease is cystic fibrosis, hemophilia B, or spinal muscular atrophy.

To that end, the modified U1snRNA molecule, the gene and/or the vector are formulated into a pharmaceutical composition comprising, in addition to the therapeutically active molecules, a pharmaceutically acceptable carrier. The selection of the carrier and of the optional pharmaceutical excipients is well within the skill of a person of ordinary skill in the art.

Another aspect of the invention is an in vitro method for restoring, in a cultured cell, the correct splicing of a target gene of therapeutic interest bearing a mutation that induces an aberrant splicing, by transfecting the cultured cell with an expression vector as defined previously.

The modified U1snRNA molecules subject of the invention were generated by using conventional molecular biology methods which are well known to a person of ordinary skill in the art. To evaluate the effects of the U1snRNAs subject of the invention on the correction of the aberrant splicing processes, and for identifying the most efficient ones, the inventors extensively used the minigene method, the application of which has been widely documented in the scientific literature. Such a method comprises cloning a gene portion bearing the mutation that causes the splicing defects into an expression vector and then transfecting the recombinant vector into in vitro cultured cells. The analysis of the transcripts originated from the portion of the gene of interest is carried out by RT-PCR, thus allowing for the identification of mRNA molecules abnormal in length derived from the aberrant splicing processes. The appearance of transcripts of interest normal in length following co-transfection of the modified U1snRNAs with the minigenes, and the sequencing thereof, represents a clear indication of the ability of the U1snRNA molecules to restore correct splicing processes.

However, the analogy between the restoration of the correct messenger RNA processing and the restoration of the final protein levels, which have the actual therapeutic significance, is not obvious.

For this reason, the inventors used the hybrid minigene method which allows for the study of the splicing, but also of the expressed protein. This method was introduced by the inventors to study a splicing mutation in the coagulation FVII (Pinotti et al., 2009). Such a method comprises cloning into an expression vector a portion of a gene containing a few introns in the region bearing the mutation that causes the splicing defect, within the entire coding sequence ("splicing-competent cDNA construct"), and subsequently transfecting the recombinant vector into in vitro cultured cells. The analysis of the transcripts originated from the portion of the gene of interest by RT-PCR, and the measurement of the levels and activity of the synthesized protein allow for the assessment of the restoration of the biological function.

The following examples are provided by way of illustration and not of limitation of the scope of the invention as defined in the appended claims.

EXAMPLE 1

Generation of the Modified U1 snRNAs

The modified U1snRNAs were generated by the following procedure: the plasmid containing the sequence of the wild-type U1-snRNA gene, that is the non-modified U1-snRNA, was digested with the BglII and BclI restriction enzymes. The sequence comprised between these two restriction sites was replaced with a double-stranded oligonucleotide comprising the binding sequence. The direct and reverse sequences of each oligonucleotide are described in Table 1 below and the resulting modified U1-snRNAs are named after the employed oligonucleotides.

Figure 2:
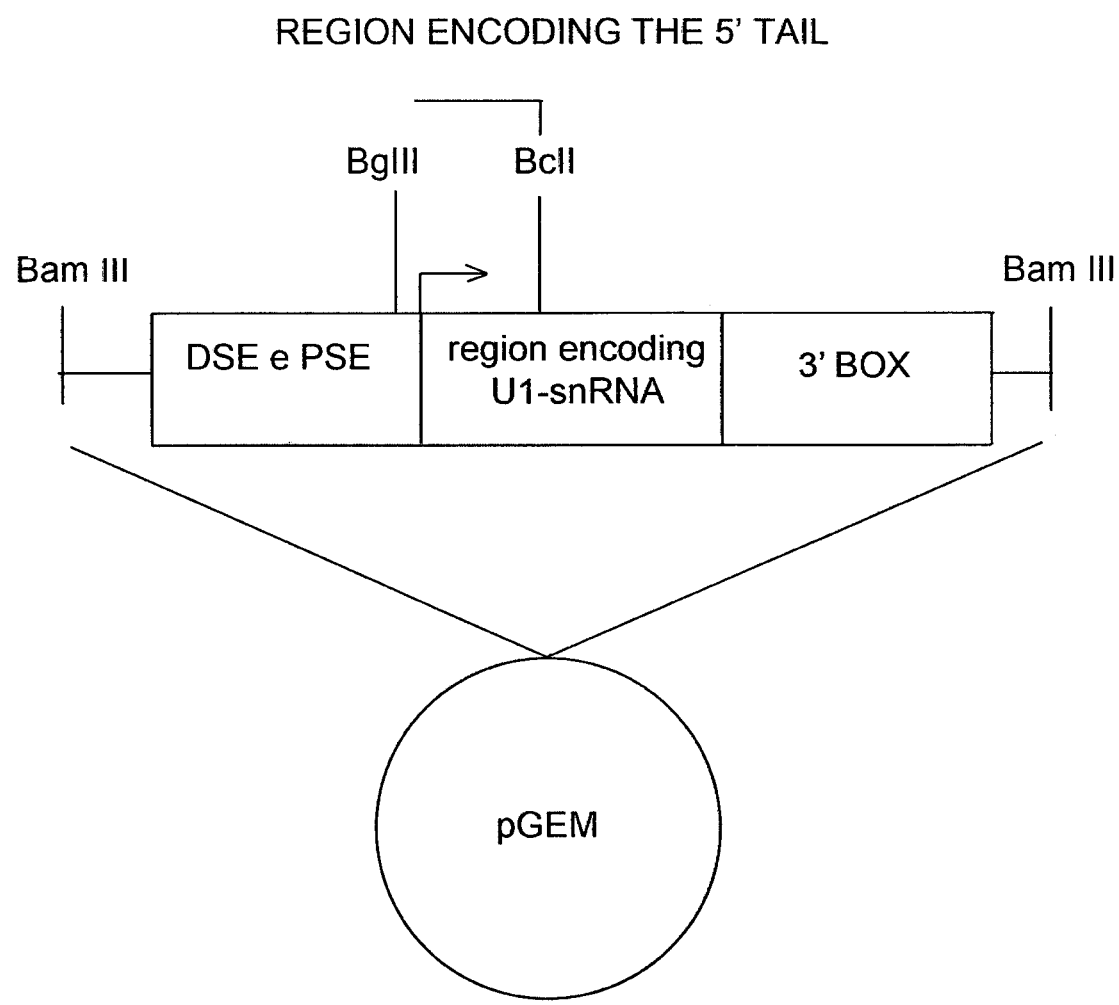
FIG. 2 illustrates the U1snRNA gene with the promoter elements DSE and PSE, the region encoding for U1snRNA (in the middle), and the 3' processing box, inserted in a plasmid vector (pGEM). The transcription start site is indicated by an arrow. The sequence between the BglII and Bcl1 restriction sites includes the region encoding for the single stranded U1snRNA tail which has been replaced by oligonucleotides that are specific for generating the modified U1snRNAs as indicated in Table 1.

Furthermore, FIG. 2 shows a schematic representation of the U1 snRNA gene elements. The cloning strategy by which the different modified U1 snRNAs were prepared is indicated. FIG. 2 shows the U1snRNA gene with the promoter elements DSE and PSE, the region encoding for U1 snRNA (in the middle), and the 3' processing box, inserted in a plasmid vector (pGEM). The transcription start site is indicated by an arrow. The sequence between the BglII and BclI restriction sites includes the region encoding for the single-stranded U1snRNA tail which has been replaced by oligonucleotides that are specific for generating the modified U1 snRNAs indicated in Table 1.

TABLE 1

| Oligonucleotides for U1 | | SEQ ID NO: |
|---|---|---|
| FIX exon 5 | | |
| FIX U1 ex5 C3T5A6 dir | GATCTCattatgacctgGCAGGGGAGATACCAT | 6 |
| FIX U1 ex5 C3T5A6 rev | gatcatggtatctcccctgccaggtcataatga | 7 |
| U1FIXex5 SH-7 dir | gatctcatatgacctgctgggcaggggagataccat | 8 |
| U1FIXex5 SH-7 rev | gatcatggtatctcccctgcccagcaggtcatatga | 9 |
| U1FIXex5 SH1 dir | gatctcatagattatgacgcaggggagataccat | 10 |
| U1FIXex5 SH1 rev | gatcatggtatctcccctgcgtcataatctatga | 11 |
| U1FIXex5 SH7 dir | gatctcatcttattcagatgcaggggagataccat | 12 |
| U1FIXex5 SH7 rev | gatcatggtatctcccctgcatctgaataagatga | 13 |
| U1FIXex5 SH9 dir | gatctcattcttattcaggcaggggagataccat | 14 |
| U1FIXex5 SH9 rev | gatcatggtatctcccctgcctgaataagaatga | 15 |
| U1FIXex5 SH10 dir | gatctcatatcttattcagcaggggagataccat | 16 |
| U1FIXex5 SH10 rev | gatcatggtatctcccctgctgaataagatatga | 17 |
| U1FIXex5 SH13 dir | gatctcataaaatcttatgcaggggagataccat | 18 |
| U1FIXex5 SH13 rev | gatcatggtatctcccctgcataagattttatga | 19 |
| U1FIXex5 SH16 dir | gatctcatataaaaaatctgcaggggagataccat | 20 |
| U1FIXex5 SH16 rev | gatcatggtatctcccctgcagattttttatatga | 21 |
| U1FIXex5 SH22 dir | gatctcatatttctttaaagcaggggagataccat | 22 |
| U1FIXex5 SH22 rev | gatcatggtatctcccctgctttaaagaaatatga | 23 |
| U1FIXex5 SH33 dir | gatctcattcagatacagagcaggggagataccat | 24 |

TABLE 1-continued

| | Oligonucleotides for U1 | SEQ ID NO: |
|---|---|---|
| U1FIXex5 SH33 rev | gatcatggtatctcccctgctctgtatctgaatga | 25 |
| U1FIXex5 SH38 dir | gatctcatagtttcagatgcaggggagataccat | 26 |
| U1FIXex5 SH38 rev | gatcatggtatctcccctgcatctgaaactatga | 27 |
| U1FIXex5 SH63 dir | gatctcatttatgtaggtgcaggggagataccat | 28 |
| U1FIXex5 SH63 rev | gatcatggtatctcccctgcacctacataaatga | 29 |
| SMN | | |
| U1ex7SMN-1G-2G-3A rev | gat cat ggt atc tcc cct gcg gag taa gtt atg a | 30 |
| U1ex7SMN-1G-2G-3A dir | gat ctc ata act tac tcc gca ggg gag ata cca t | 31 |
| U1ex7SMN sh2 rev | gat cat ggt atc tcc cct gct aag tct gct atg a | 32 |
| U1ex7SMN sh2 dir | gat ctc ata gca gac tta gca ggg gag ata cca t | 33 |
| U1ex7SMN sh17 rev | gat cat ggt atc tcc cct gct atg aaa gtt atg a | 34 |
| U1ex7SMN sh17 dir | gat ctc ata act ttc ata gca ggg gag ata cca t | 35 |
| CFTR exon 12 | | |
| U1 -1A 4T dir | gatctcatacatacttggcaggggagataccat | 36 |
| U1 -1A 4T rev | gatcatggtatctcccctgccaagtatgtatga | 37 |
| U1 G3 T4 dir | gatctcatacacacctggcaggggagataccat | 38 |
| U1 G3 T4 REV | gatcatggtatctcccctgccaggtgtgtatga | 39 |
| U1 T4 A5 dir | gatctcatatatacctggcaggggagataccat | 40 |
| U1 T4 A5 REV | gatcatggtatctcccctgccaggtatatatga | 41 |
| U1 CF sh+1 dir | gatctctcaaagaacatacgcaggggagataccat | 42 |
| U1 CF sh+1 REV | gatcatggtatctcccctgcgtatgttctttgaga | 43 |
| CF12 SH+9 Dir | gatctcataggtattcaaagcaggggagataccat | 44 |
| CF12 SH+9 Rev | gatcatggtatctcccctgctttgaatacctatga | 45 |
| CF12 SH+11 Dir | gatctcataagtaaggtattcagcaggggagataccat | 46 |
| CF12 SH+11 Rev | gatcatggtatctcccctgctgaataccttacttatga | 47 |
| CF12 SH+33 DIR | gatcatggtatctcccctgctcatgctaaaataga | 48 |
| CF12 SH+33 REV | gatctctattttagcatgagcaggggagataccat | 49 |

EXAMPLE 2

Transfection of the Minigenes into Cultured Cells and Analysis of the Splicing Products The containing-vectors were inserted into the cells by transient transfection with Lipofectamine (liposomes). Following extraction of total cellular RNA with Trizol, the RNA was analyzed by RT-PCR with specific primers.

The reaction occurs in two steps: the RNA inverse transcription into a cDNA strand by a reverse transcriptase using random primers as templates, and amplification of the obtained cDNA by a DNA polymerase.

The PCR reaction was carried out in a final volume of 25 μl of a mixture containing:

- 5 μl of AMV/Tfl 5× buffer suitable for the correct functioning of both the enzymes mentioned above;
- 1 μl of 10 mM dNTPs mix;
- 50 pmol of forward primer and 50 pmol of reverse primer;
- 2 μl 25 mM MgSO$_4$;
- 2 μl of cell-extracted RNA;
- 1 μl of AMV-RT (0.1μ/μl), 1 μl of Tfl DNA polymerase;
- ultra pure H$_2$O q.s.

The reverse transcription step was performed at 45° C. for 45 min. A step wherein the PCR mix was adjusted to the temperature of 94° C. for 2 min. was then carried out, followed by 40 rounds of PCR, and finally by an extension step for 7 sec at 68° C.

The amplification products were separated by electrophoresis in an agarose gel and/or run by capillary electrophoresis.

EXAMPLE 3

Exonic Mutations Near the Donor Site and Mutations in the Poly-Pyrimidine Sequence Upstream of the Exon 5 Acceptor Site of the Coagulation Factor IX Associated with Hemophilia B In the factor IX gene (F9), the exonic mutations at position −2 within the donor site, as well as the mutations at positions −8 and −9 within the acceptor site of exon 5, are associated with hemophilia B. It is interesting to note that the mutations at position −2 in the exon are synonymous and do not modify the coding sequence but induce exon skipping and therefore they are classifiable as splicing mutations. The mutations at positions −8 and −9 within the acceptor site also induce skipping of exon 5.

Table 2 shows the mutations under discussion which were identified in patients affected by hemophilia B (Hemophilia B International database). Nucleotides belonging to exon 5 are shown in capital letters, whereas those belonging to the intron are in lower case. Each position, shown at the bottom of the figure, is affected by one or more mutations, the nucleotide change of which is shown in bold.

TABLE 2

| Position | Nucleotide substitution | Sequence of the acceptor/donor site Positions: −12 to −1\ +1 to +6 |
|---|---|---|
| Acceptor site | −8 | T > G | tgctgcttttag\ATG (SEQ ID NO: 69) |
| | −9 | T > G | tgcgtcttttag\ATG (SEQ ID NO: 70) |

TABLE 2-continued

| Position | Nucleotide substitution | Sequence of the acceptor/donor site Positions: −12 to −1\ +1 to +6 |
|---|---|---|
| Donor site | −2 | A > C | CCG\gtcata |
| | −2 | A > G | CGG\gtcata |
| | −2 | A > T | CTG\gtcata |

A vector for the expression of a minigene construct designated as pTB NdeI FIX was constructed to study the splicing of normal and mutated FIX. To do this, a portion of genomic DNA 308 bp upstream of exon 5 and 283 bp downstream of the region affected by the mutations was inserted into a vector widely used to study in vitro splicing, plasmid pTBNdeI (Pagani et al., 2000; Pagani et al 2002; Pagani et al., 2003).

Figure 3:
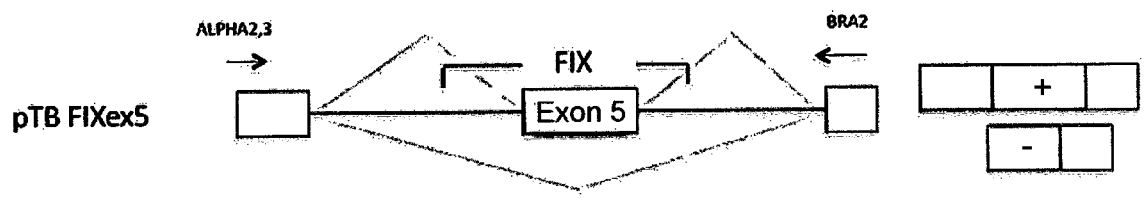
FIG. 3 schematically illustrates the middle portion of construct pTB FIX ex5 used for studying splicing.

In FIG. 3, the middle portion of construct pTB FIX ex5 used for studying splicing is represented schematically. The rectangles represent the middle regions of the construct of a globin and of FIX exon 5, with the introns represented as lines. Exon 5 and the flanking intronic regions (IVS4 and IVS5) were cloned into plasmid pTB. The transcription is under the control of the α globin promoter and of the SV40 enhancer. The two possible splicing isoforms are indicated.

Figure 4:
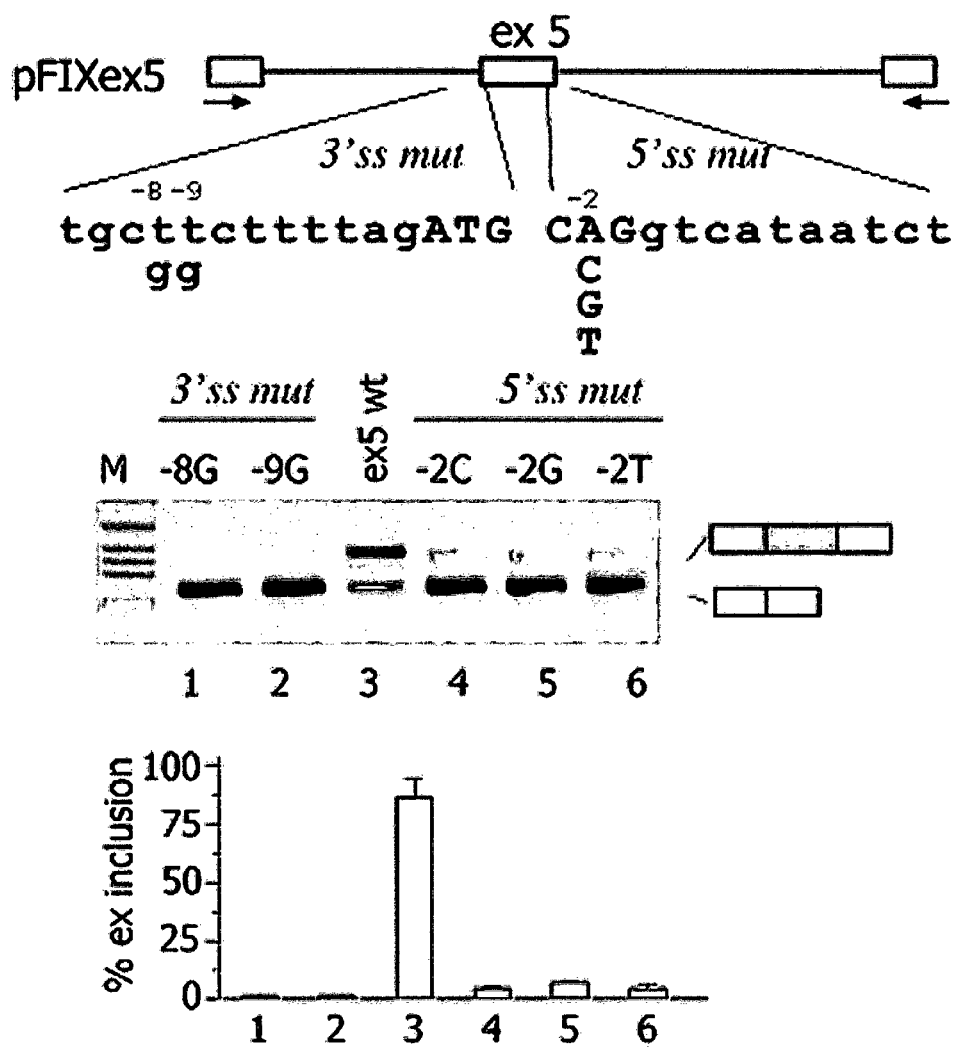
FIG. 4 illustrates the effects of the expression of minigenes generated in HepG2 eukaryotic cells. The vectors were inserted into the cells by transient transfection and the RNA was analyzed as indicated in the appended method, by using oligonucleotides alfa2-3 and BRA2 as the primers. The illustrated sequences represent the sequences of the acceptor/donor site, with possible mutation(s) as listed by Table 2, hereinbelow. The sequence on the left side of the figure is SEQ ID NO: 64. The sequence on the right side of the figure is SEQ ID NO: 65.

After inserting the mutations, the inventors have then demonstrated the causative effect thereof by the expression of minigenes generated in HepG2 eukaryotic cells, an ideal cell model for studying proteins of hepatic origin, such as FIX. In particular, the vectors were inserted into the cells by transient transfection and the RNA was analyzed as indicated in the appended method, by using oligonucleotides alfa2-3 and BRA2 as the primers. Specifically, all the mutations induce exon skipping (FIG. 4).

The list of the modified U1-snRNAs created, the target sequences thereof and the localization thereof around the donor site are reported in Table 3.

TABLE 3

Binding sequences of the modified U1-snRNAs for the correction of the splicing defects of exon 5 of the factor IX gene

| FIX U1 snRNAs | Binding sequence (5' > 3') | Target sequence (5'→3') | Length (bp) | SEQ ID NO: |
|---|---|---|---|---|
| C3T5A6 | uaugaccug | caggtcata | 9 | 58 |
| FIX-7 | ugaccugcugg | ccagcaggtca | 11 | 50 |
| FIX1 | agauuaugac | gtcataatct | 10 | 1 |
| FIX7 | ucuuauucaga | tctgaataaga | 11 | 2 |
| FIX9 | ucuuauuca | tgaataaga | 9 | 51 |
| FIX10 | aucuuauuc | gaataagat | 9 | 52 |
| FIX13 | aaaaucuu a | taagatttt | 9 | 53 |
| FIX16 | uaaaaaauc | gatttttta | 9 | 54 |
| FIX22 | uuucuuuaa | ttaaagaaa | 9 | 55 |
| FIX33 | auucagauacaga | tctgtatctgaat | 13 | 71 |
| FIX38 | auaguuucagau | atctgaaactat | 12 | 72 |
| FIX63 | auuuauguaggu | acctacataaat | 12 | 73 |

The localization of the binding sites on the modified U1 snRNAs employed for the correction of exon 5 splicing defects of the clotting factor IX gene is shown in FIG. 5. The sequence of exon 5 is indicated in capital letters, whereas the remaining sequence indicates the intron.

Figure 6:
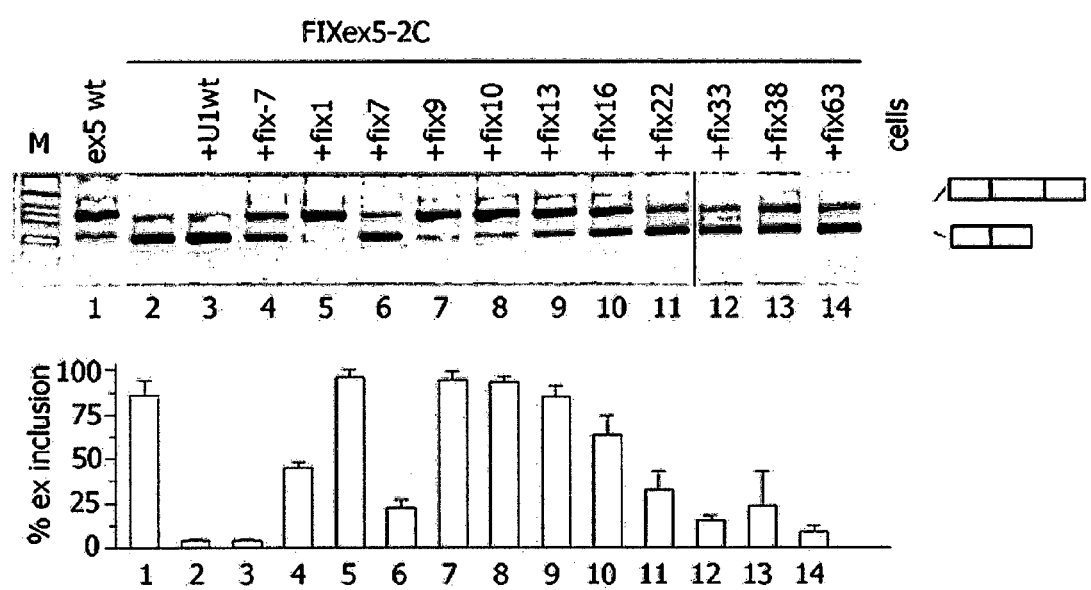
FIG. 6 illustrates different modified U1snRNAs that were tested on the mutation at position −2C, and their effect on the percentage of exon 5 inclusion.

The different modified U1 snRNAs were tested on the mutation at position −2C, and their effect on the percentage of exon 5 inclusion is shown in FIG. 6. As can be observed, many modified U1 snRNAs are able to significantly increase the percentage of exon 5 inclusion, thereby compensating for the effects of the mutation at position −2C. This indicates that the binding of U1 snRNA to the donor site or nearby (ExSpeU1) favors the definition of exon 5. The efficiency depends on the position, and the U1-FIX1, FIX9, FIX10 show a higher activity. The efficiency decreases with increasing distance from the 5'ss splicing site. It is important to note that the U1 snRNA complementarity to non-conserved intronic sequences flanking the splicing site is important for increasing the specificity thereof. Moreover, it must be pointed out that even small increases in FIX (>2% of normal) would result in a significant improvement of patients' hemorrhagic tendency. For this reason, even the less efficient ExSpeU1 molecules may have a therapeutic significance in hemophilia B, as well as in other clotting defects. With the modified U1snRNA molecules analogous effects were achieved with the other mutations within the donor site (−2A>G, −2A>T) and the acceptor site (−8T>G, −9T>G).

Particularly noteworthy is the demonstration that one single modified U1snRNA, and particularly the one that pairs at position 9 (FIX9), is able to significantly restore splicing in the presence of all the different mutations investigated.

Figure 7:
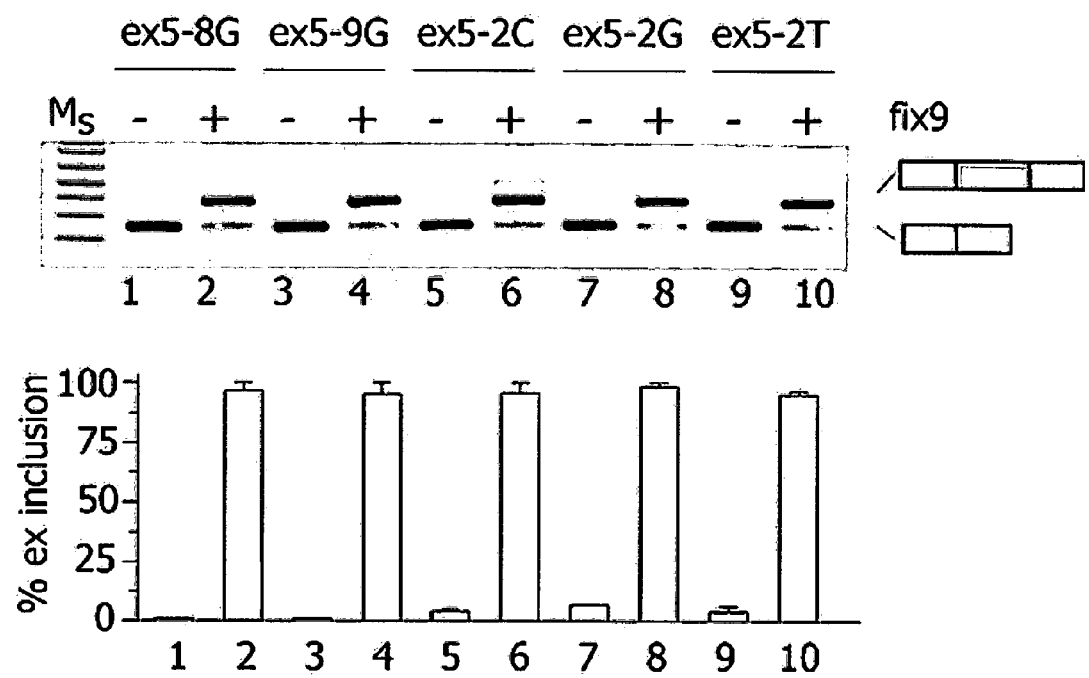
FIG. 7 illustrates results from Example 3, showing that one single modified U1snRNA, and particularly the one that pairs at position 9 (FIX9), is able to significantly restore splicing in the presence of all the different mutations investigated.

The data related to this finding, never reported till now, are shown in FIG. 7.

The effectiveness of any therapeutic approach is testified by the ability thereof to induce protein synthesis, the levels of which are decreased under the pathological conditions.

Figure 8:
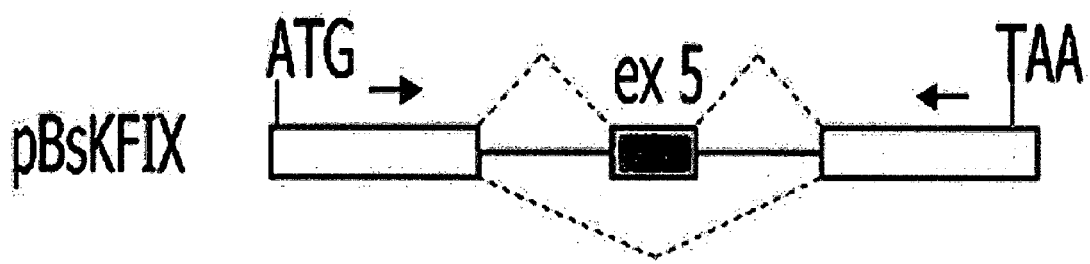
FIG. 8 illustrates a construct wherein a minigene was created in which exon 5 and its flanking intronic sequences have been inserted into the FIX full-length encoding sequence, and cloned into vector pBskFIX. The rectangles indicate the coding sequences, with the ATG start codon and the TAA stop codon, whereas the introns are shown as lines.

To verify if the correction observed at the messenger RNA level results in an increased synthesis and function of secreted FIX, a minigene was created in which exon 5 and its flanking intronic sequences have been inserted into the FIX full-length encoding sequence. FIG. 8 schematically reports the construct generated for this study and cloned into vector pBsk-FIX. The rectangles indicate the coding sequences, with the ATG start codon and the TAA stop codon, whereas the introns are reported as lines.

Figure 9:
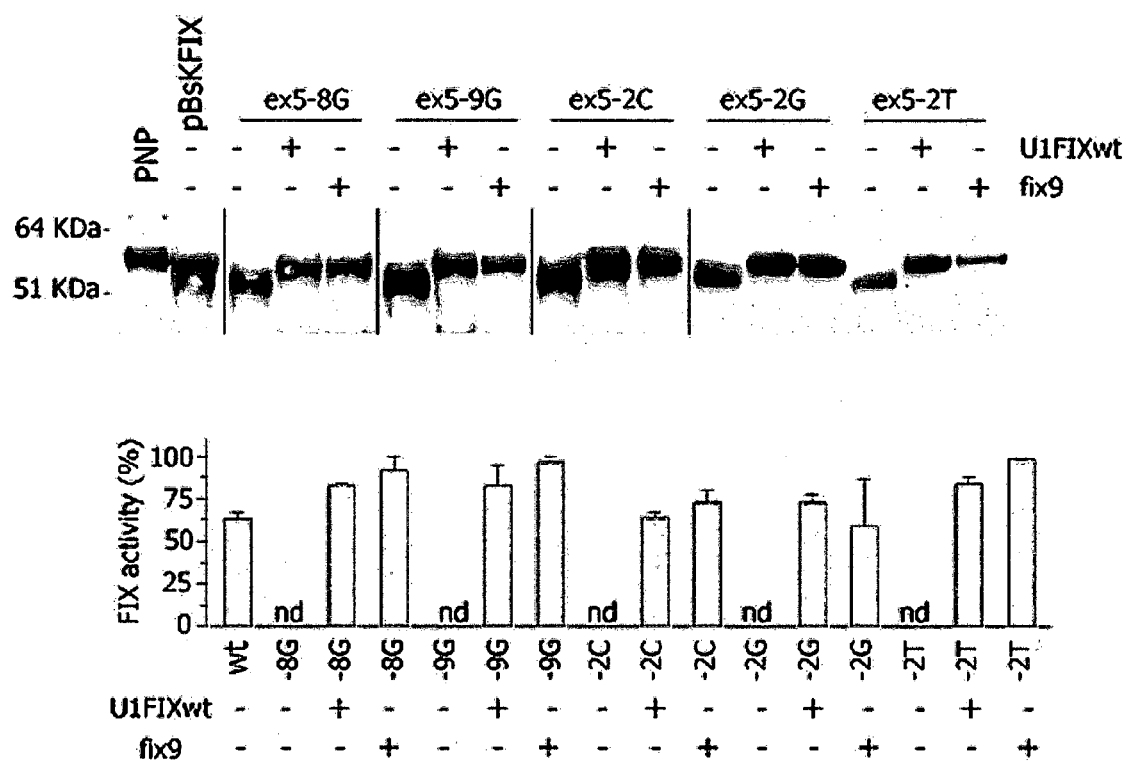
FIG. 9 illustrates the results of transfecting the minigene illustrated by FIG. 8 into BHK hamster kidney cells, selected for their ability to synthesize and secrete a functional FIX, demonstrating that the messenger RNA is correctly processed and translated into protein.

Transfection of this minigene into BHK hamster kidney cells, selected for their ability to synthesize and secrete a functional FIX, demonstrated that the messenger RNA is correctly processed and translated into protein (FIG. 9). In fact, considerable amounts of functional protein are measured in the culture medium. By contrast, mutations in the donor site (−2A>G, −2A>T) or in the acceptor site (−8T>G, −9T>G) cause exclusion of exon 5 and synthesis of a truncated protein variant not functional in a normal clotting assay. By Western blotting (upper panel), the mutation was actually proven to cause synthesis of a FIX variant having a lower molecular weight, due to the absence of exon 5 in the coding sequence. No appreciable clotting activity corresponds to this form (lower panel).

Expression of the intronic ExSpeU1 fix9 is able to restore splicing and increase the levels of functional secreted FIX up to levels that, if reached in patients, would be largely above the therapeutic threshold. These results confirm the effectiveness of the ExSpeU1 approach.

EXAMPLE 4

Spinal Muscular Atrophy

Vectors expressing the SMN1 (pCI-SMN1) and SMN2 (pCI-SMN2) minigenes were used for the study (Hua et al., 2007). Such minigenes are widely used to validate the effect of therapeutic molecules capable of correcting the splicing defect in the SMN2 gene (Hua et al., 2007; Hua et al., 2008).

Figure 10:
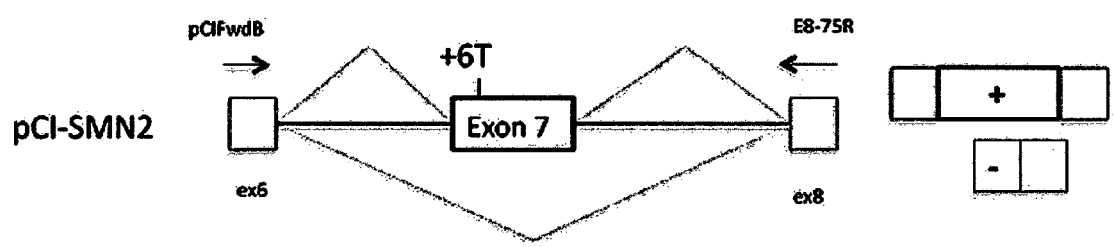
FIG. 10 schematically illustrates the pCI-SMN2 minigene.

The two minigenes are composed of 111 nucleotides of exon 6, 200 nucleotides of intron 6, the 54 nucleotides of exon 7, the 444 nucleotides of intron 7, and the first 75 nucleotides of exon 8, under the control of the CMV promoter. The two minigenes differ for the presence of one nucleotide substitution at position 6 in exon 7. In pCI-SMN1 there is a C, whereas in pCI-SMN2 there is a T. Such a synonymous substitution induces a splicing defect in pCI-SMN2 with skipping of exon 7 in the mature transcript. The pCI-SMN2 minigene is schematically represented in FIG. 10. The synonymous variant at position +6T in the exon, which induces exon skipping, is indicated.

Many experimental evidences have demonstrated that the correction of the splicing in the SMN2 gene represents an effective therapeutic strategy in SMA (Hua et al., 2007; Hua et al., 2008; Lorson et al., 2010). Table 5 shows a list of the generated modified U1-snRNAs, the target sequences thereof, and their localization around the donor site. The different modified U1-snRNAs and their effect on the percentage of exon 7 inclusion were tested in the SMN2 minigene and as a control in the SMN1 minigene.

TABLE 5

Recognition sequences (U1-SR) in the gene for the modified U1-snRNAs for the correction of the splicing defect of exon 7 in the SMN2 gene

| SMN U1-snRNAs | Binding sequence (5'→3') | Target sequence (5'→3') | Length (bp) | SEQ ID NO: |
|---|---|---|---|---|
| -1G-2G-3A | acuuacucc | ggagtaagt | 9 | 60 |
| SMN_SH2 | gcagacuua | taagtctgc | 9 | 56 |
| SMN_SH17 | acuuucaua | tatgaaagt | 9 | 57 |

Figure 11:
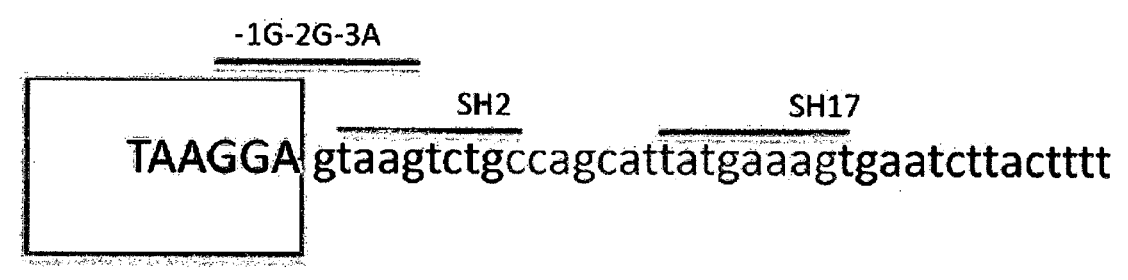

FIG. 11 shows the localization of the modified SMN U1 snRNAs employed for correcting the splicing defect of the SMN2 gene.

The minigenes were inserted into HeLa cells by transient transfection with Lipofectamine (liposomes). The RNA was analyzed by RT-PCR as indicated in Example 2. The RNA extracted from the cells was then subjected to RT-PCR with primers pCIFwdB and E8-75 R to assess the splicing products.

Figure 12:
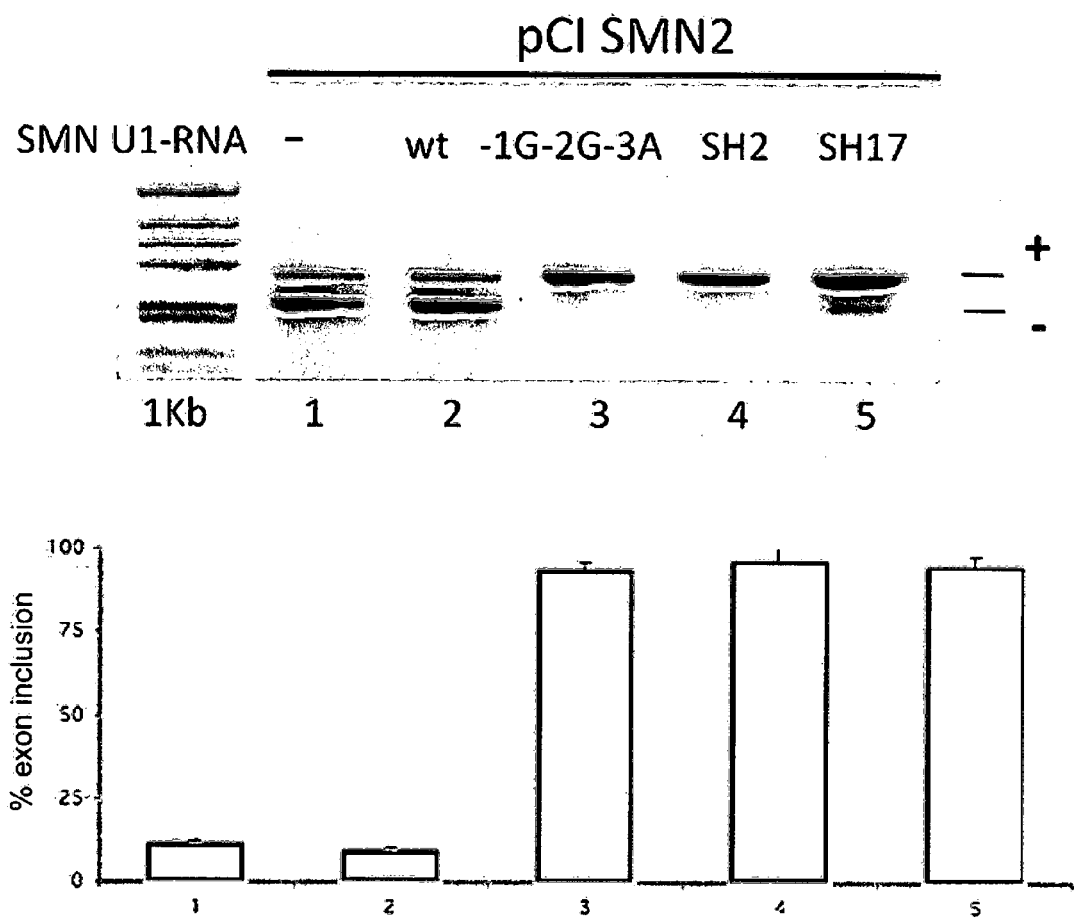
FIG. 12 illustrates the effect of modified SMN U1s on SMN2 splicing. The splicing profile of exon 7 of the SMN2 gene (well 1) and the effect of co-expression of the modified U1 snRNAs (wells 2-5) are indicated in the upper part of the figure. The two exon 7 inclusion (+) and exclusion (−) isoforms are indicated. In the lower panel the histogram shows the percentage of inclusion of exon 7, and thus, of the correct splicing. The data are the average of three independent experiments.

As can be observed in FIG. 12, transfection of the pCI SMN2 plasmid into cultured cells mainly shows skipping of exon 7. Co-transfection with the U1-Wt control plasmid (well 2) has no effect. Co-transfection of the U1ex7SMN-1G-2G-3A (well 3), U1ex7SMN sh2 (well 4), and U1ex7SMN sh17 (well 5) plasmids induces a significant increase in the percentage of inclusion of exon 7. Co-transfection of the different modified SMN U1 snRNAs in the SMN1 control plasmid showed no effect.

In particular, FIG. 12 shows the effect of the modified SMN U1s on SMN2 splicing. The splicing profile of exon 7 of the SMN2 gene (well 1) and the effect of co-expression of the modified U1 snRNAs (wells 2-5) are indicated in the upper part of the figure. The two exon 7 inclusion (+) and exclusion (−) isoforms are indicated. In the lower panel the histogram shows the percentage of inclusion of exon 7, and thus, of the correct splicing. The data are the average of three independent experiments.

EXAMPLE 5

Mutations in the Exon and CFTR Exon 12 Donor Site Associated with Cystic Fibrosis Cystic fibrosis is caused by mutations in the CFTR gene. Mutations localized in exon 12 splicing site, associated with serious disease forms, which induce aberrant exon skipping are indicated in Table 6. A few mutations localized in exon 12 induce exon skipping (Pagani et al., 2003). Exonic mutations that induce exclusion of exon 12 are indicated in Table 7.

TABLE 6

List of mutations in exon 12 donor site of the CFTR gene.
The mutations are shown in bold

| Position | Nucleotide substitution | Sequence of CF exon 12 donor site Positions: −3 −2 −1\ +1 +2 +3 +4 +5 +6 |
|---|---|---|
| −1 | G > A | AAA\gtatgt |
| −1 | G > T | AAT\gtatgt |
| +3 | A > G | AAG\gtgtgt |
| +3 | A > C | AAG\gtctgt |
| +5 | T > A | AAG\gtatat |

TABLE 7

| Nucleotide substitution | Amino acid substitution | Position in the exon |
|---|---|---|
| G > A | A566T | +17 |
| C > T | Y577Y | +52 |

Table 8 shows the recognition sequence in the U1-snRNA gene modified for the correction of the splicing defects in exon 12 of the CFTR gene, which was selected from a larger panel of modified U1 snRNAs.

TABLE 8

| CFTR U1-snRNAs | Binding Sequence (5'→3') | Target Sequence (5'→3') | Length (bp) | SEQ ID NO: |
|---|---|---|---|---|
| cf11 | AUAAGUAAGGUAUUCA | TGAATACCTTACTTAT | 16 | 4 |

Figure 13:
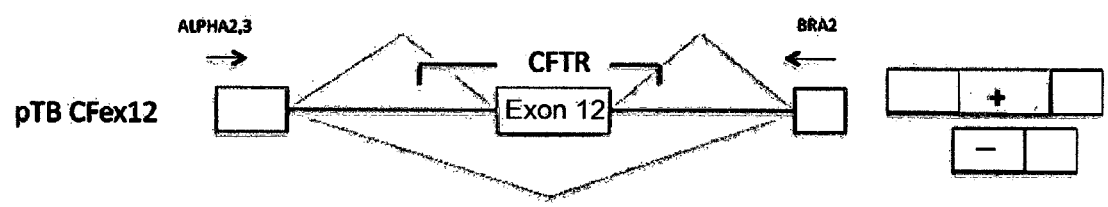
FIG. 13 schematically illustrates the pTB CFex12 minigene (Pagani et al., 2003). The rectangles represent the middle regions of the a-globin construct, and of the CFTR exon 12, with introns represented as lines. Exon 12 and the flanking intronic regions were cloned into plasmid pTB. The transcription is under the control of the a-globin promoter and SV 40 enhancer. The two possible splicing isoforms are indicated.

The pTB CFex12 minigene employed is schematically represented in FIG. 13 (Pagani et al., 2003). The rectangles represent the middle regions of the α-globin construct, and of the CFTR exon 12, with introns represented as lines. Exon 12 and the flanking intronic regions were cloned into plasmid pTB. The transcription is under the control of the α-globin promoter and SV40 enhancer. The two possible splicing isoforms are indicated.

FIG. 14 shows the localization of the ExSpeU1 cf11 that was used for correcting the splicing defects of exon 12 of the CFTR gene.

The RNA was analyzed by RT-PCR as indicated in Example 2: transfection of the minigenes into cultured cells and analysis of the splicing products, by using alfa2-3 and BRA2 as the primers and the minigene.

Figure 15:
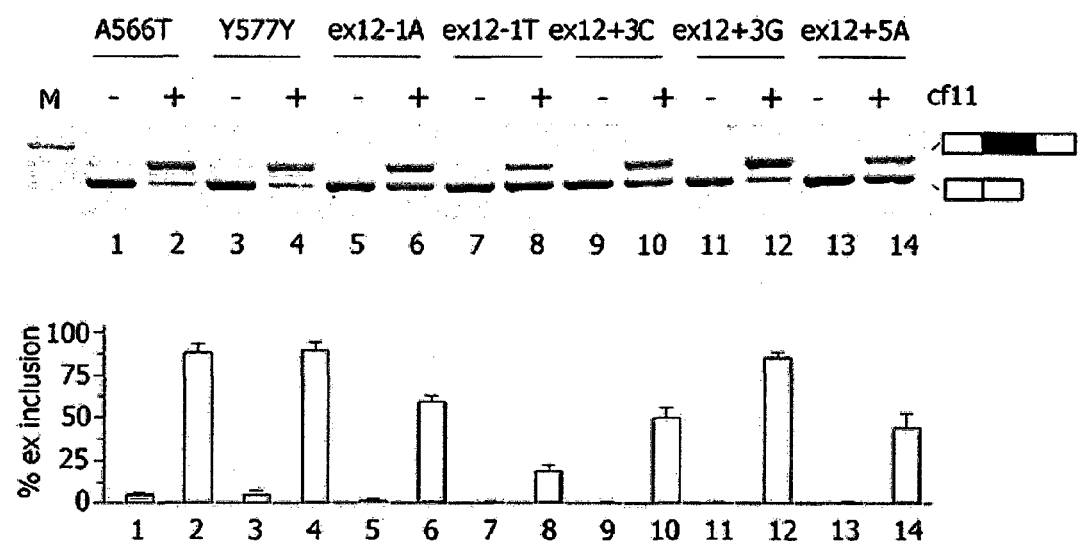
FIG. 15 illustrates the effect of ExSPeU1 cf11 on the aberrant splicing induced by different types of mutations localized in the 5'ss and in the exon. ExSPeU1 cf11 induces a significant increase in the percentage of inclusion of exon 12 in all the mutants analyzed.

FIG. 15 shows the effect of ExSPeU1 cf11 on the aberrant splicing induced by different types of mutations localized in the 5' ss and in the exon. ExSPeU1 cf11 induces a significant increase in the percentage of inclusion of exon 12 in all the mutants analyzed.

The splicing profile of the different variants (odd wells) and the effect of co-expression of ExSPeU1 cf11 (even wells) are indicated in the upper part of FIG. 15. The two exon 12 inclusion (+) and exclusion (−) isoforms are indicated. In the lower panel the histogram shows the percentage of inclusion of exon 12, and thus, of the correct splicing. The data are the average of 3 independent experiments.

The cells were transfected with 0.5 μg of vectors expressing each specific variant. The splicing profile was assessed by RT-PCR with primers ALPHA2,3 and BRA2. The amplified fragments were separated on a 2% agarose gel. The identity of the transcripts including (+) or excluding (−) exon 12 is indicated on the right-hand side of the gel and has been validated by sequencing.

REFERENCES

Cartegni, L., S. L. Chew, and A. R. Krainer. 2002. Listening to silence and understanding nonsense: exonic mutations that affect splicing. Nat Rev Genet 3:285-98.

Horowitz D S, Krainer A R. Mechanisms for selecting 5' splice sites in mammalian pre-mRNA splicing. Trends Genet. 1994 March; 10(3):100-6.

Hua, Y., T. A. Vickers, B. F. Baker, C. F. Bennett, and A. R. Krainer. 2007. Enhancement of SMN2 exon 7 inclusion by antisense oligonucleotides targeting the exon. PLoS Biol 5:e73.

Hua, Y., T. A. Vickers, H. L. Okunola, C. F. Bennett, and A. R. Krainer. 2008. Antisense masking of an hnRNP A1/A2 intronic splicing silencer corrects SMN2 splicing in transgenic mice. Am J Hum Genet 82:834-48.

Lorson, C. L., H. Rindt, and M. Shababi. Spinal muscular atrophy: mechanisms and therapeutic strategies. Hum Mol Genet 19:R111-8.

Pagani, F., E. Buratti, C. Stuani, M. Romano, E. Zuccato, M. Niksic, L. Giglio, D. Faraguna, and F. E. Baralle. 2000. Splicing factors induce cystic fibrosis transmembrane regulator exon 9 skipping through a nonevolutionary conserved intronic element. J Biol Chem 275:21041-7.

Pagani, F., E. Buratti, C. Stuani, R. Bendix, T. Dork, and F. E. Baralle. 2002. A new type of mutation causes a splicing defect in ATM. Nat Genet 30:426-9.

Pagani, F., C. Stuani, M. Tzetis, E. Kanavakis, A. Efthymiadou, S. Doudounakis, T. Casals, and F. E. Baralle. 2003. New type of disease causing mutations: the example of the composite exonic regulatory elements of splicing in CFTR exon 12. Hum Mol Genet 12:1111-20.

Pagani, F., and F. E. Baralle. 2004. Genomic variants in exons and introns: identifying the splicing spoilers. Nat Rev Genet 5:389-96.

Pinotti, M., L. Rizzotto, D. Balestra, M. A. Lewandowska, N. Cavallari, G. Marchetti, F. Bernardi and F. Paganil. Maestri, F. Pagani, and F. Bernardi. 2008. U1-snRNA mediated rescue of mRNA processing in severe factor VII deficiency. Blood 111:2681-2684

Pinotti, M., D. Balestra, L. Rizzotto, I. Maestri, F. Pagani, and F. Bernardi. 2009. Rescue of coagulation factor VII function by the U1+5A snRNA. Blood 113:6461:6464

The invention claimed is:

1. A modified human U1snRNA molecule, capable of correcting the skipping of an exon caused by a mutation localized in the sequence comprised between 50 base pairs upstream and 20 base pairs downstream of an exon, the modified human U1snRNA molecule wherein a portion of the single-stranded nucleotide sequence of the 5' region of the wild-type human U1snRNA is replaced by a single-stranded binding nucleotide sequence, wherein the binding nucleotide sequence is selected from the group consisting of SEQ ID NOs: 1, 2, 51, 52, 53, 54, 55, 56 and 57.

2. The modified human U1snRNA molecule according to claim 1, wherein the portion of the 5' region which is replaced by the binding nucleotide sequence is 9 to 11 nucleotides in length.

3. A method of treating a genetic disease caused by or associated with exon skipping, the method comprising administering the modified human U1snRNA molecule according to claim 1 to a patient in need thereof, thereby treating the disease caused by or associated with exon skipping, wherein the genetic disease is cystic fibrosis, hemophilia B or spinal muscular atrophy.

4. An isolated gene encoding for a modified human U1snRNA molecule according to claim 1.

5. The isolated gene according to claim 4, comprising a promoter sequence and a polyadenylation signal sequence.

6. The isolated gene according to claim 5, wherein the promoter is the endogenous promoter of the gene encoding for human U1snRNA.

7. A method of treating a genetic disease caused by exon skipping, comprising administering the isolated gene according to claim 4 to a patient in need thereof, thereby treating the disease caused by or associated with exon skipping, wherein the genetic disease is cystic fibrosis, hemophilia B or spinal muscular atrophy.

8. An expression vector comprising an isolated gene according to claim 4.

9. The expression vector according to claim 8, which is an adeno-associated viral vector.

10. A method of treating a genetic disease caused by or associated with exon skipping, the method comprising administering the expression vector according to claim 9 to a patient in need thereof, thereby treating the disease caused by or associated with exon skipping, wherein the genetic disease is cystic fibrosis, hemophilia B or spinal muscular atrophy.

11. A pharmaceutical composition comprising a modified human U1snRNA molecule according to claim 1 and a pharmaceutically acceptable carrier.

12. An in vitro method to restore in a cultured cell the correct splicing of a target gene of therapeutic interest bearing a mutation which induces exon skipping, comprising transfecting the cultured cell with an expression vector according to claim 8, thereby upregulating a function of and/or the expression of the target gene of therapeutic interest in the cultured cell, wherein the target gene of therapeutic interest is a gene for cystic fibrosis, hemophilia B or spinal muscular atrophy.

13. A pharmaceutical composition comprising an isolated gene according to claim 4 and a pharmaceutically acceptable carrier.

14. A pharmaceutical composition comprising an expression vector according to claim 8 and a pharmaceutically acceptable carrier.

* * * * *